United States Patent
Swanson

(10) Patent No.: US 8,533,944 B2
(45) Date of Patent: Sep. 17, 2013

(54) METHOD FOR FABRICATION OF A NEUROSTIMULATON LEAD INCLUDING MULTIPLE MICRO-CABLES

(75) Inventor: John Swanson, Lake Oswego, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 321 days.

(21) Appl. No.: 12/962,421

(22) Filed: Dec. 7, 2010

(65) Prior Publication Data

US 2011/0137382 A1    Jun. 9, 2011

Related U.S. Application Data

(60) Provisional application No. 61/267,275, filed on Dec. 7, 2009.

(51) Int. Cl.
*H01R 43/00* (2006.01)

(52) U.S. Cl.
USPC ............ 29/857; 29/33 F; 29/828; 174/113 R; 174/126.2; 607/116

(58) Field of Classification Search
USPC .................. 29/33 F, 825, 282, 857, 861, 867; 57/10, 17, 18; 174/113 R, 126.2, 128.1; 600/373; 607/116, 119, 122
See application file for complete search history.

(56) References Cited

U.S. PATENT DOCUMENTS

| | | | |
|---|---|---|---|
| 5,476,495 A | 12/1995 | Kordis et al. | |
| 5,760,341 A * | 6/1998 | Laske et al. | ................ 174/126.2 |
| 5,796,044 A * | 8/1998 | Cobian et al. | ................. 607/119 |
| 7,287,366 B2 * | 10/2007 | Dye et al. | ........................... 57/10 |
| 7,555,349 B2 | 6/2009 | Wessman et al. | |
| 2005/0027339 A1 | 2/2005 | Schrom et al. | |
| 2005/0027340 A1 | 2/2005 | Schrom et al. | |
| 2005/0027341 A1 | 2/2005 | Schrom et al. | |
| 2006/0041295 A1 | 2/2006 | Osypka | |
| 2006/0089691 A1 | 4/2006 | Kaplan et al. | |
| 2006/0089695 A1 | 4/2006 | Bolea et al. | |
| 2006/0089697 A1 | 4/2006 | Cross et al. | |
| 2007/0282411 A1 * | 12/2007 | Franz et al. | .................... 607/116 |
| 2011/0072658 A1 * | 3/2011 | Dye et al. | ....................... 29/33 F |

* cited by examiner

*Primary Examiner* — Donghai D Nguyen

(57) ABSTRACT

In one embodiment, a method of fabricating a stimulation lead for stimulation of tissue of a patient, the method comprises: providing a plurality of cables, wherein each of the cables comprises a plurality of wires twisted about a core support and disposed within an outer sheath, wherein each of the plurality of wires comprises a coating of insulative material to electrically isolate each wire from each other wire within the respective cable, each of the plurality of wires being disposed in a single layer circumferentially about a central axis of the respective cable; wrapping the plurality of cables about a central core in a helical manner to form a cable assembly.

8 Claims, 3 Drawing Sheets

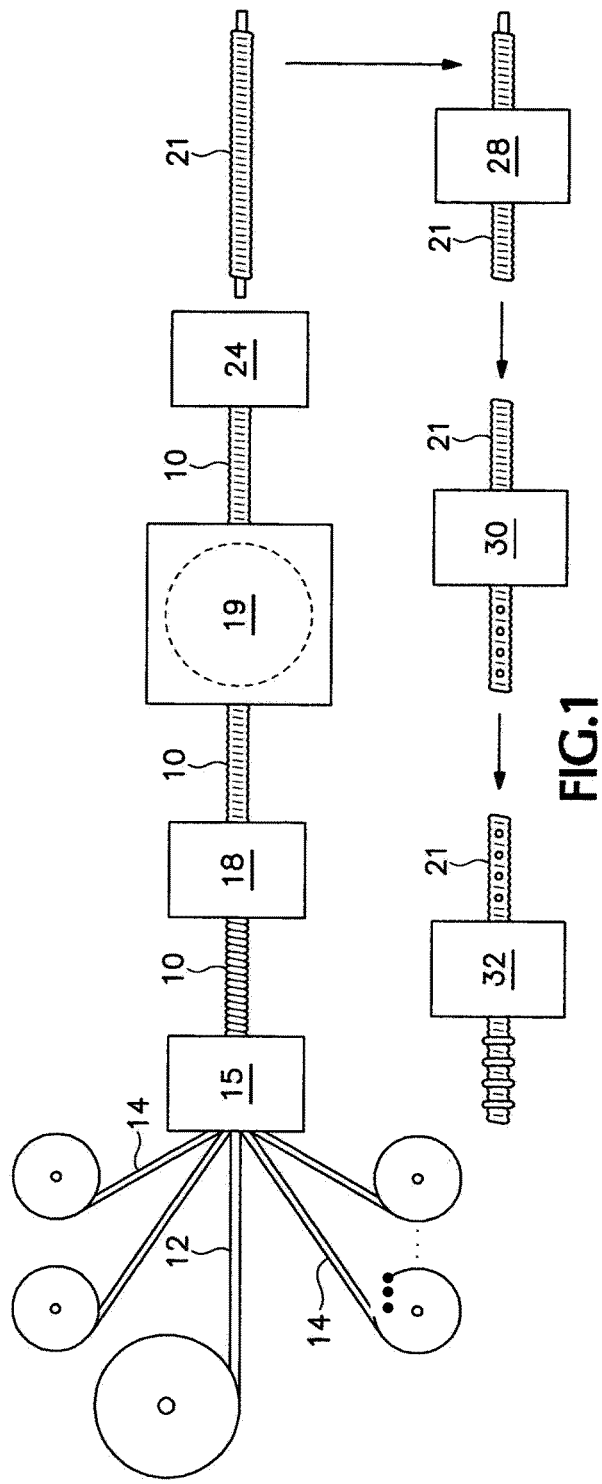
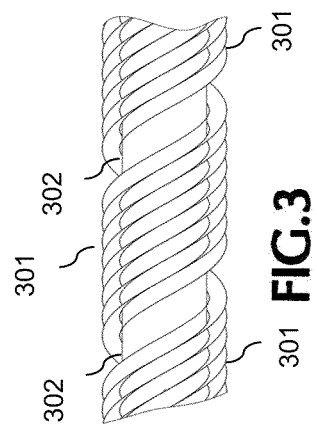
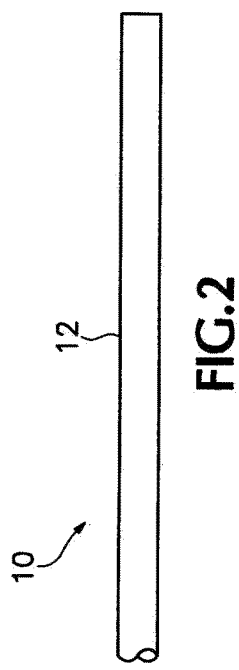
FIG.1
FIG.2
FIG.3

METHOD FOR FABRICATION OF A NEUROSTIMULATON LEAD INCLUDING MULTIPLE MICRO-CABLES

CROSS-REFERENCE TO RELATED APPLICATIONS

This application claims the benefit of U.S. Provisional Application No. 61/267,275, filed Dec. 7, 2009, which is incorporated herein by reference.

TECHNICAL FIELD

This application is generally related to a stimulation lead for stimulation of tissue of a patient and a method of fabricating the same.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. Applying electrical energy to the spinal cord associated with regions of the body afflicted with chronic pain can induce "paresthesia" (a subjective sensation of numbness or tingling) in the afflicted bodily regions which can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator.

Each stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted at the location adjacent or within the tissue to be electrically stimulated. The proximal end of the stimulation lead is connected to the header of the pulse generator or to an intermediate "extension" lead.

In certain cases, it is desirable to use a larger number of conductor wires within the lead body to permit the use of a larger number of electrodes. For example, deep brain stimulation leads may employ multiple groups of segmented electrodes disposed axially from the distal tip of the stimulation lead. The segmented electrodes enable greater directional control of the stimulation field. Also, cortical leads and paddle leads may employ larger numbers of electrodes.

Fabrication of lead bodies with larger numbers of conductor wires can be a relatively complex process. In one known fabrication process, a first layer of conductor wires are wound about a mandrel and, then, a second layer of conductor wires are wound about the first layer to form the lead body of the stimulation lead. During the wire winding process, insulative material is provided to embed the conductor wires. Electrode attachment occurs by exposing individual conductor wires by removing insulative material from the lead body. However, exposing an individual conductor wire within the interior layer without exposing any of the other wires can be challenging and time consuming. Accordingly, manufacturing costs can be excessive and manufacturing yields can be less than optimal.

SUMMARY

In one embodiment, a method of fabricating a stimulation lead for stimulation of tissue of a patient, the method comprises: providing a plurality of cables, wherein each of the cables comprises a plurality of wires twisted about a core support and disposed within an outer sheath, wherein each of the plurality of wires comprises a coating of insulative material to electrically isolate each wire from each other wire within the respective cable, each of the plurality of wires being disposed in a single layer circumferentially about a central axis of the respective cable; wrapping the plurality of cables about a central core in a helical manner to form a cable assembly, wherein during the wrapping each cable of the plurality of cables is rotated so that each wire of a respective cable is disposed at an exterior surface of the cable assembly at respective axial positions of the cable assembly; providing an outer insulative layer over the cable assembly; forming a lead body assembly from the cable assembly; and fabricating a plurality of electrodes and terminals that are electrically coupled to wires of the plurality of cables of the lead body assembly to form a stimulation lead.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 1 depicts a process for fabricating a stimulation lead according to one representative embodiment.

FIG. 2 depicts a stainless steel mandrel for use in the process of FIG. 1.

FIG. 3 depicts a portion of a lead body in a side view according to one representative embodiment.

DETAILED DESCRIPTION

Figure 4:
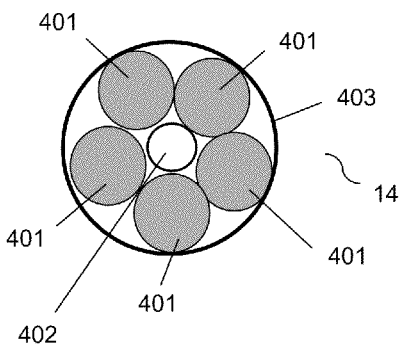
FIG. 4 depicts a micro cable for use in fabricating a lead body according to one representative embodiment.

In one embodiment, a process for fabricating lead body material for stimulation leads begins with a continuous working material 10 shown in FIG. 1. In one embodiment, the working material 10 is a polytetrafluoroethylene (PTFE) coated stainless steel mandrel wire 12 (shown in FIG. 2). Referring again to FIG. 1, the working material 10 is then helically wrapped with a set of micro cables 14 at a wire wrapping system 15. While seven micro cables 14 are used in one embodiment, those skilled in the art will recognize that any suitable number of micro cables 14 may be wrapped onto mandrel 12 according to other embodiments.

In one preferred embodiment, micro cables 14 are wrapped about working material 10 in an axially repeating pattern of groups 301 of closely spaced wires with each group 301 separated by distance 302 that is larger than the spacing between adjacent wires within each group (FIG. 3). The distance between groups in FIG. 3 is by way of example and any suitable distance may be employed according to some embodiments. The wrapping of micro cables 14 in this manner may occur using the wire wrapping system disclosed in U.S. patent application Ser. No. 61/247,264, entitled "SYSTEM AND METHOD FOR FABRICATING A STIMULATION LEAD," which is incorporated herein by reference.

Referring again to FIG. 1, in step 18, an outer sheath is provided over the working material 10 (which now includes the helically wound micro cables 14) using any suitable method. Upon provision of the outer sheath of insulative material, working material 10 may now be spooled and later unspooled (not shown) or fed directly to the next step in the process. In the next step, working material 10 may optionally be heated in reflow oven 19. Micro cables 14 are heated to a temperature that causes insulative material of micro cables 14 to approach or achieve a phase change, thereby becoming soft and adherent and ultimately fusing together, by heating, melting and re-solidifying.

At this point, the working material 10, now comprising mandrel 12 having micro cables 14 at least partially fused about it, may now be spooled onto a spool and stored for later work. Continuous working material 10 is cut (step 24) into individual lead bodies 21. Each individual lead body 21 may have a length anywhere from about 10 cm (4 in) to about 150 cm (60 in).

After the lead bodies 21 have been cut to length, mandrel 12 is removed from within in a mandrel removal step 28. This task may be facilitated by a coating of mandrel 12 that will ease removal, such as a PTFE coating. The mandrel removal step 28 may be a simple hand operation by a human worker.

Next, in an electrode creation step 30, electrodes and terminals are provided on the distal and proximal ends of the lead body, respectively. Any suitable technique or process may be employed to provide the electrodes and terminals. Also, the lead body could alternatively be connected to a paddle structure which holds electrodes in a planar arrangement as is well known in the art.

Micro cable 14 is shown in greater detail in FIG. 4. A length of micro cable 14 is preferably fabricated by using a standard serving process (using any suitable commercially available serving system) to twist stranded wires or other suitable conductors 401 around center support core 402. Center support core 402 may be a monofilament or a metallic wire as examples. Each conductor 401 may be a stranded wire (e.g. of a diameter of approximately 0.003 inches) coated with a thin coating of insulative material with suitable properties (a perfluoroalkoxy copolymer (PFA), polytetrafluoroethylene, liquid crystal polymer (LCP), etc.). In one embodiment, the coating is perfluoroalkoxyethylene. In one embodiment, five conductors 401 are wound about central support core 402, although any suitable number of conductors 401 may employed depending upon the total number of conductors selected for the final lead configuration. Outer sheath 403 of insulative material is then provided about the wound conductors 401 (e.g., using an extrusion process). In one embodiment, the diameter of micro cable 14 is approximately 0.012 inches. The length of micro cable 14 is then cut into separate segments and wound onto respective spools.

Figure 5:
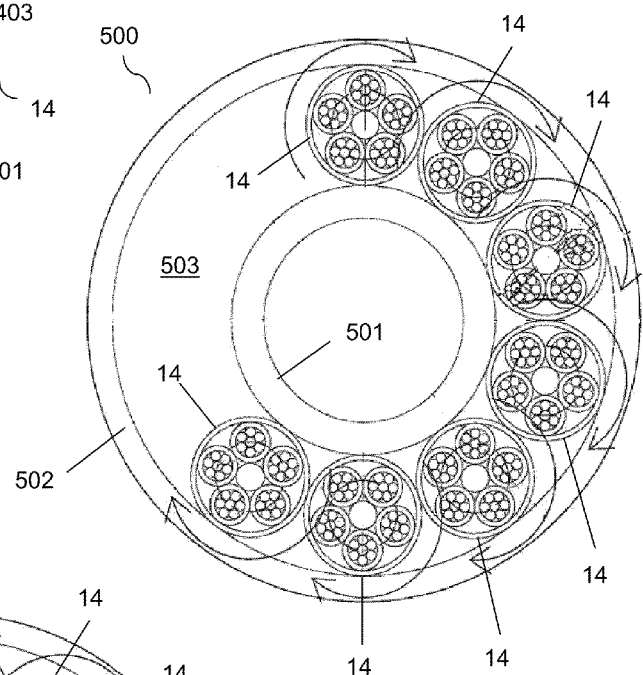
FIG. 5 depicts a lead body according to one representative embodiment.

FIG. 5 depicts lead body assembly 500 according to one representative embodiment. In this embodiment, seven micro cables 14 are helically wound about inner wall 501 of insulative material, although any suitable number could be employed. As depicted in FIG. 5, each conductor 401 within each micro cable 14 is twisted so that the conductors 401 rotate with each micro cable 14 to expose a different conductor 401 at each different axial position along lead body 500. That is, a different conductor 401 within each micro cable 14 is closest to exterior insulative sheath 502 at different axial positions along lead body 500. This is achieved by using a suitable wire wrapping system to twist conductors 401 about central support core 402. Also, as shown in FIG. 5, gap 503 is provided that is empty of micro cables 14. The presence of gap 503 facilitates the elongation of lead body 500 according to some embodiments.

In one embodiment, the diameter of lead body 500 is approximately 0.055 inches which is approximately equal to the diameter of commercially available neurostimulation leads. However, lead body 500 encloses 35 conductors for connection to electrodes and terminals, which is considerably larger than known commercially available neurostimulation leads adapted for long term implantation. Also, because each conductor 401 within each micro cable 14 is located near the surface of lead body 500 at various points, access to each conductor 401 for electrode and terminal fabrication is relatively straight forward and only involves removal of a small amount of insulation from sheath 502 (i.e., it is not necessary to ablate through insulative material to a separate interior layer). In some embodiments, different visual characteristics (e.g., different colors) may be employed to permit an operator to distinguish between respective conductors 401 within each cable 14.

The dimensions for lead body 500 and components thereof are by way of example. Other suitable dimensions may be employed. Also, other configurations of conductor 401 and micro cables 14 may be employed. For example, 4 conductor/8 micro cables or 6 conductor/6 micro cables may be selected for other embodiments.

Further, in some embodiments, lead body 500 is fabricated such that lead body 500 is capable of elastic elongation under relatively low stretching forces. Also, after removal of the stretching force, lead body 500 is capable of resuming its original length and profile. For example, in one embodiment, relatively low durometer, elastic polymer material (e.g. CARBOSIL™) is used for inner wall 501 and outer sheath 502. The combination of the selection of the insulative materials, the helically wrapping of the micro cables, and the repeating groups of micro cables with separating gaps enables the stretching according to the relatively low stretching forces. For example, the lead body may stretch 10%, 20%, 25%, 35%, or even up to 50% at forces of about 0.5, 1.0, and/or 2.0 pounds of stretching force. For additional description of a lead body capable of elastic elongation, reference is made to U.S. Patent Publication No. 2007/0282411, entitled "COMPLIANT ELECTRICAL STIMULATION LEADS AND METHODS OF FABRICATION," which is incorporated herein by reference.

Figure 6:
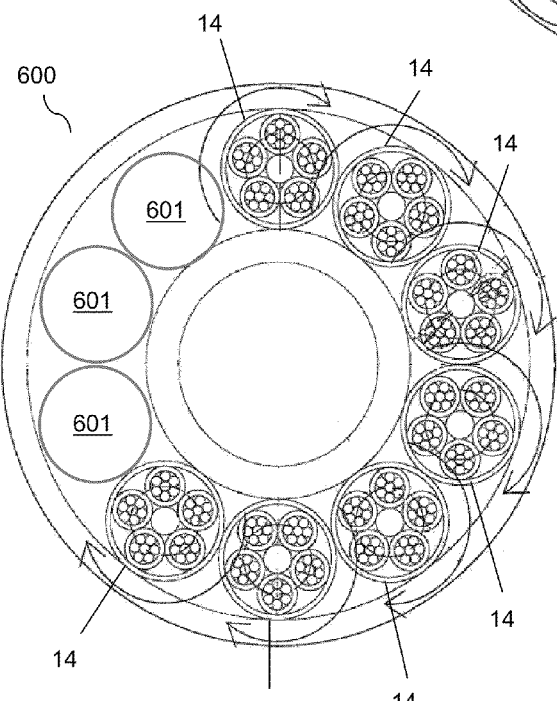
FIG. 6 depicts another lead body according to one representative embodiment.

FIG. 6 depicts lead body 600 according to one representative embodiment. Lead body 600 is substantially similar to lead body 500 except that in lieu of gap 503, lead body 600 includes a plurality of elastic spacer threads 601 wound about inner wall 501 with micro cables 14. The elastic spacer threads facilitate the elastic characteristics of lead body 600 while ensuring that micro cables 14 remain in their respective angular positions within lead body 600. The elastic spacer threads may be subsequently fused with the insulative material of inner wall 501 and outer sheath 502 using suitable application of heat and, optionally, pressure to form a uniform fused matrix of insulative material enclosing conductors 401 according to some embodiments.

Figure 7B:
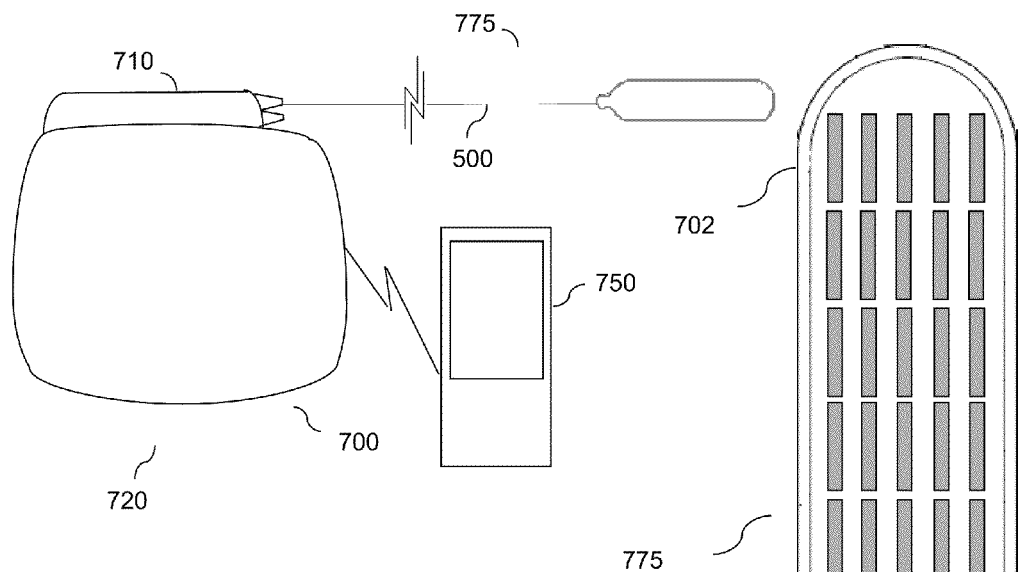
FIG. 7B depicts a stimulation system according to one representative embodiment.
Figure 7A:
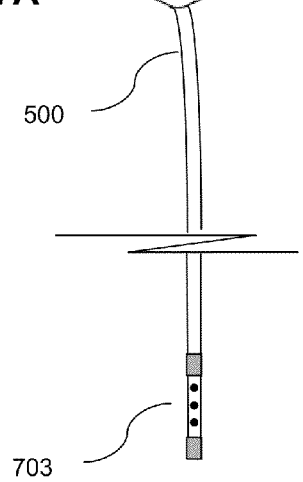
FIG. 7A depicts a stimulation lead according to one representative embodiment.

FIG. 7A depicts cortical paddle lead 775 according to one representative embodiment. Cortical paddle lead 775 comprises a relatively large number of electrodes 701 disposed on paddle structure 702. The larger number of electrode sites for selection by a clinician may be beneficial for cortical stimulation in which targeting the appropriate cortical tissue can be challenging. Electrodes 701 are electrically coupled to terminals 703 through the conductors 401 (not shown in FIG. 7) of lead body 500 (or any other lead body according to some representative embodiments). Although a cortical paddle is shown in FIG. 7A, any suitable stimulation lead for stimulation of tissue of a patient may utilize lead bodies according to some representative embodiments. For example, spinal cord stimulation leads, deep brain stimulation leads, peripheral nerve stimulation leads, cardiac leads may employ lead bodies according to some embodiments described herein. Also, any suitable number and arrangement of electrodes may be employed according to other embodiments. For example, ring electrodes or segmented electrodes may be disposed about the outer diameter of lead body 500 in lieu of being disposed on paddle structure 702.

FIG. 7B depicts stimulation system 700 according to one representative embodiment. Neurostimulation system 700 includes pulse generator 720 and one or more stimulation leads 775. Pulse generator 720 is typically implemented using a metallic housing that encloses circuitry for generating the electrical pulses for application to neural tissue of the patient. Control circuitry, communication circuitry, and a rechargeable battery (not shown) are also typically included within pulse generator 720. Pulse generator 720 is usually implanted within a subcutaneous pocket created under the skin by a physician.

Lead 775 is electrically coupled to the circuitry within pulse generator 720 using header 710. Lead 775 includes terminals 703 (shown in FIG. 7A) that are adapted to electrically connect with electrical connectors (e.g., "Bal-Seal" connectors which are commercially available and widely known) disposed within header 710. The terminals 703 are electrically coupled to conductors (not shown in FIG. 7B) within lead body 500 of lead 775. The conductors conduct pulses from the proximal end to the distal end of lead 775. The conductors are also electrically coupled to electrodes 701 to apply the pulses to tissue of the patient. Lead 775 can be utilized for any suitable stimulation therapy. An "extension" lead (not shown) may be utilized as an intermediate connector if deemed appropriate by the physician.

Pulse generator 720 preferably wirelessly communicates with programmer device 750. Programmer device 750 enables a clinician to control the pulse generating operations of pulse generator 720. The clinician can select electrode combinations, pulse amplitude, pulse width, frequency parameters, and/or the like using the user interface of programmer device 750. The parameters can be defined in terms of "stim sets," "stimulation programs," (which are known in the art) or any other suitable format. Programmer device 750 responds by communicating the parameters to pulse generator 720 and pulse generator 720 modifies its operations to generate stimulation pulses according to the communicated parameters.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating a stimulation lead for stimulation of tissue of a patient, the method comprising:
providing a plurality of cables, wherein each of the cables comprises a plurality of wires twisted about a core support and disposed within an outer sheath, wherein each of the plurality of wires comprises a coating of insulative material to electrically isolate each wire from each other wire within the respective cable, each of the plurality of wires being disposed in a single layer circumferentially about a central axis of the respective cable;
wrapping the plurality of cables about a central core in a helical manner to form a cable assembly, wherein during the wrapping each cable of the plurality of cables is rotated so that each wire of a respective cable is disposed at an exterior surface of the cable assembly at respective axial positions of the cable assembly;
providing an outer insulative layer over the cable assembly;
forming a lead body assembly from the cable assembly; and
fabricating a plurality of electrodes and terminals that are electrically coupled to the plurality of wires of the plurality of cables of the lead body assembly to form the stimulation lead.

2. The method of claim 1 wherein the fabricating comprises:
exposing each wire in the lead body assembly by removing insulative material at the exterior surface of the lead body assembly.

3. The method of claim 1 wherein the wrapping comprises:
wrapping the plurality of cables in a repeating pattern of respective sets of closely spaced cables with adjacent sets of cables separated by a gap that is greater than a distance between adjacent cables within each set.

4. The method of claim 1 wherein the wrapping comprises:
wrapping the plurality of cables uniformly about a circumference of the central core.

5. The method of claim 1 wherein each of the plurality of wires comprises a stranded wire covered with a coating of perfluoroalkoxy copolymer (PFA).

6. The method of claim 1 wherein the outer sheath of each cable is formed of a thermoplastic silicone polycarbonate urethane.

7. The method of claim 1 further comprising:
heating the cable assembly and the outer insulative layer to fuse insulative material of the outer sheath of each cable of the plurality of cables with insulative material of the outer insulative layer to form the lead body assembly.

8. The method of claim 1 further comprising:
wrapping a plurality of insulative spacer threads in with the plurality of cables.

* * * * *